United States Patent [19]

Ackerman et al.

[11] Patent Number: 4,558,279

[45] Date of Patent: Dec. 10, 1985

[54] METHODS FOR DETECTING AND IMAGING A TEMPERATURE OF AN OBJECT BY NUCLEAR MAGNETIC RESONANCE

[75] Inventors: Jerome L. Ackerman; Leland C. Clark, Jr.; Stephen R. Thomas, all of Cincinnati, Ohio

[73] Assignees: University of Cincinnati; Children's Hospital Research Foundation, both of Cincinnati, Ohio

[21] Appl. No.: 472,675

[22] Filed: Mar. 7, 1983

[51] Int. Cl.$^4$ .............................................. G01R 33/08
[52] U.S. Cl. ...................................... 324/315; 324/300
[58] Field of Search ............... 324/300, 307, 315, 318, 324/322, 309

[56] References Cited

U.S. PATENT DOCUMENTS

| | | | |
|---|---|---|---|
| 4,297,637 | 10/1981 | Crooks et al. | 324/309 |
| 4,318,043 | 3/1982 | Crooks et al. | 324/309 |
| 4,319,190 | 3/1982 | Brown | 324/309 |
| 4,361,807 | 11/1982 | Burl | 324/309 |
| 4,442,404 | 4/1984 | Bergmann | 324/315 |

OTHER PUBLICATIONS

Pearson, Deuterium Lock-Channel Nuclear Magnetic Resonance Thermometers for Multinuclear Spectrometers, Analytical Chemistry, vol. 50, No. 12, Oct. 1978, pp. 1717 to 1719.
Gadian, D. G.: Nuclear Magnetic Resonance and its Applications to Living Systems, 1st Edition, Oxford: Clarendon Press, pp. 23-42, (1982).
Moon, R. B. and Richards, J. H.: Determination of Intracelluclar pH by $^{31}$p Magnetic Resonance, J. Biological Chemistry, 218(20): 7276-7278, (Oct. 25, 1973).
Kramer, D. M.: Imaging of Elements Other than Hydrogen, in Kaufman, L., Crooks, L. E. and Margulis, A. R.: Nuclear Magnetic Resonance Imaging in Medicine, 1st Edition, New York-Tokyo: Igaku-Shoin, Ltd. pp. 184-203, (1981).
Holland, G. N. et al.: $^{19}$F Magnetic Resonance Imaging, J. Magnetic Resonance, 28: 133-136, (1977).
Thomas, S. R. et al.: Nuclear Magnetic Resonance Imaging Techniques as Developed Modestly within a University Medical Center Environment: What Can the Small System Contribute at this Point? Magnetic Resonance Imaging, 1(1): 11-21, (1981).
Delpuech, J. J., Hamza, M. A., and Serratrice, G.: Determination of Oxygen, by a Nuclear Magnetic Resonance Method, J. Magnetic Resonance, 36: 173-179, (1979).
Hamza, N. A. et al.: Fluorocarbons as Oxygen Carriers, II, An NMR Study of Partially or Totally Fluorinated Alkanes and Alkenes, J. Magnetic Resonance, 42: 227-241, (1981).
Roberts, J. D.: Studies of Confirmational Equilibria and Equilibration by Nuclear Magnetic Resonance Spectroscopy, Chemsitry in Britain, 2: 529-535, (1966).
Homer, J. and Thomas, L. F.: Nuclear Magnetic Resonance Spectra of Cyclic Fluorocarbons, Trans. Faraday Soc. 59: 2431-2443, (1963).
Sternhell, S.: Kinetic $^{13}$C NMR Thermometer, Texas A & M University NMR Newsletter, No. 285: 21-23, (Jun. 1982).
Bornais, Jr. and Brownstein, S.: A Low Temperature Thermometer for $^1$H, $^{19}$F and $^{13}$, J. Magnetic Resonance, 29: 207-211, (1978).
Hall, L. D. and Sukuman, S.: Chemical Microscopy Using a High-Resolution, NMR Spectrometer, a Combination of Tomography/Spectroscopy Using Either $^1$H or $^{13}$C, 50: 161-164, (1982).
Lauterbur et al.: Zeugmatograhic High Resolution Nuclear Magnetic Resonance Spectroscopy Images of Chemical Inhomogeneity within Macroscopic Objects, J. American Chemical Society, 97(23): 6866-6868, Nov. 12, 1975.

*Primary Examiner*—Michael J. Tokar
*Attorney, Agent, or Firm*—Wood, Herron & Evans

[57] ABSTRACT

A novel and improved method to detect indirectly a temperature of an object employing nuclear magnetic resonance techniques (NMR). The method involves obtaining an NMR spectrum to determine chemical shift, relaxation times, spin-spin couplings or quadrupole couplings for an element of a compound having at least one conformational isomer wherein the compound is influenced by a temperature of the object. Uniquely, the present invention may detect temperature in the body of an animal. Further, the present invention discloses a novel method to determine and monitor thermal physiological states in an animal as well as determine and monitor thermal states in an object. Because of the unique and advantageous non-invasive, non-destructive and non-ionizing properties, the present invention may be employed in an object or animal continuously. The present invention also provides for the thermal imaging, or NMR thermography, by one-, two-, or three-dimensional reconstruction techniques from chemical shift, relaxation times, (e.g., $T_1$ or $T_2$,) spin-spin couplings and quadrupole couplings for an element of a compound having at least one conformational isomer in an object or animal influenced by a temperature in the object or animal. The methods disclosed are applicable to inanimate and animate solids.

54 Claims, No Drawings

METHODS FOR DETECTING AND IMAGING A TEMPERATURE OF AN OBJECT BY NUCLEAR MAGNETIC RESONANCE

BACKGROUND OF THE INVENTION

Nuclear magnetic resonance, hereinafter NMR, is relatively a recent method in radiology with respect to the study and imaging of intact biological systems. Like X-rays and ultrasound procedures, NMR is a non-invasive analytical technique employed as a means to examine a body. Unlike X-rays, however, NMR is a non-ionizing, non-destructive process that can be employed continuously to a host. Further, NMR imaging is capable of providing anatomical information comparable to that supplied by X-ray CAT scans. In comparison to ultrasound, the quality of projections or images reconstructed from currently known NMR techniques either rival or transcend those observed with ultrasound procedures. Thus, these rather unusual and highly desirable characteristics provide NMR with present potential to be one of the most versatile and useful diagnosing tools ever used in biological and medical communities today.

Basically, NMR is a process that results when nuclei with magnetic moments are subjected to a magnetic field. If electromagnetic radiation in the radio-frequency region of the spectrum is subsequently applied, the magnetized nuclei will emit a detectable signal having a frequency similar to the one applied.

More specifically, NMR predicates on the fact that many nuclei have an intrinsic magnetism resulting from an angular momentum, or spin, of such nuclei. Resembling a bar magnet, the spin property generates a magnetic dipole, or magnetic moment, around such nuclei. Thus, when two external fields are applied to an object, the strong magnetic field causes the dipoles for such nuclei, e.g., nuclei with spin designated $\frac{1}{2}$, to align either parallel or anti-parallel with said magnetic field. Of the two orientations, the parallel alignment requires the nuclei to store less energy and hence is the stable or preferred orientation. As to the second applied field, comprising radio-frequency waves of a precise frequency or quantum of electromagnetic radiation, it will cause such nuclei to nutate or flip into the less stable orientation. In an attempt to re-establish the preferred parallel or stable orientation, the excited nuclei will emit electromagnetic radio waves at a frequency nominally proportional to the magnitude of the strong field, but specifically characteristic of their chemical environment.

Thus, the NMR technique detects radio-frequency signals emitted from nuclei as a result of a process undergone by such nuclei when exposed to at least two externally applied fields. If a third magnetic field in the form of a gradient is applied, nuclei with the same magnetogyric constant will nutate at different frequencies, i.e., Larmor frequencies, depending upon the location within the object. Thus, similar nuclei in an object can be detected discriminately for a particular region in said object according to their Larmor frequency corresponding to a particular magnetic field strength along the applied magnetic gradient, as demonstrated by the following equation $f_o = (\gamma) H_o$ wherein $f_o$ is the Larmor frequency, $\gamma$ is the magnetogyric constant, and $H_o$ is the applied magnetic field.

Unfortunately, there are several factors that may limit the usefulness of NMR applications in vivo. In general, NMR is an insensitive radiologic modality requiring significant amounts of nuclei with magnetic moments to be present in an object. Consequently, not all nuclei in vivo are present in sufficient quantities to be detected by present NMR techniques. Further, not all nuclei in vivo have magnetic moments. Some of the more common isotopes that do not have magnetic moments which are found in vivo include carbon-12, oxygen-16 and sulfur-32. Thus, current NMR applications in vivo are restricted to those nuclei that have magnetic moments and are sufficiently abundant to overcome the insensitivity of present NMR techniques.

Heretofore, NMR applications in vivo have almost invariably been concerned with imaging or detecting the water distribution within a region of interest derived from the detection of proton resonance. Other nuclei not only have lower intrinsic NMR sensitivities, but also are less abundant in biological material. Consideration has, however, been given to the use of other nuclei such as phosphorus-31 which represents the next best choice for NMR in vivo applications due to its natural and abundant occurrence in biological fluids. For example, phosphorus-31 NMR has been found to provide an indirect means for determining intracellular pH and $Mg^{++}$ concentration simply by measuring the chemical shift of the inorganic phosphate resonance in vivo and determining from a standard titration curve the pH or $Mg^{++}$ concentration to which the chemical shift corresponds. The type of information available from NMR. IN: Gadian, D.G.: *Nuclear Magnetic Resonance and Its Applications to Living Systems.* First Edition. Oxford: Clarendon Press. pp. 23–42 (1982); Moon, R. B. and Richards, J. H.: Determination of Intracellular pH By $^{31}P$ Magnetic Resonance. *J. Biological Chemistry.* 218(20):7276–7278 (Oct. 25, 1973). In addition, sodium-23 has been used to image a heart perfused with a medium containing 145 mM sodium in vivo. Unfortunately, difficulties with these nuclei arise because of the inherent sensitivity losses due to the lower resonant frequencies of these nuclei. Moon, R. B. and Richards, J. H.: Determination of Intracellular pH By $^{31}P$ Magnetic Resonance. *J. Biological Chemistry.* 218(20):7276–7278 (Oct. 25, 1973).

Another stable element which is uniquely suited for NMR imaging is fluorine because its intrinsic sensitivity practically commensurates with that of protons, it has a spin of $\frac{1}{2}$, so as to give relatively uncomplicated, well-resolved spectra, its natural isotopic abundance is 100 percent, it gives large chemical shifts, and because its magnetogyric constant is similar to that of protons, the same equipment can be used. Unfortunately, fluorine NMR applications in vivo are in effect not conducted due to the practical non-existence in biological materials of fluorine observable by NMR methods normally employed in studying biological systems. However, nuclear medicine procedures using the positron emitter fluorine-18 are well documented and include, for example, bone scanning, brain metabolism and infarct investigations using fluorodeoxyglucose, and myocardial blood flow and metabolism. With respect to fluorine NMR imaging, some investigations into such applications have been made. Suggestions have been presented involving the study of vascular system disorders, in conjunction with fluorocarbon blood substitutes, Holland, G. N. et al: $^{19}F$ Magnetic Resonance Imaging. *J. Magnetic Resonance.* 28:133–136 (1977), and the localization/kinetics of fluorocarbon following liquid breathing. Further, in vitro canine studies investigating the feasibility of fluorine as an agent for NMR imaging of myocardial infarction have also been performed. The above cited principles and studies directed to flourine are acknowledged in Thomas, S. R. et al: Nuclear Magnetic Resonance Imaging Techniques Developed Modestly Within a University Medical Center Environment: What Can the Small System Contribute at this Point? *Magnetic Resonance Imaging.* 1(1):11–21 (1981). Further, an NMR technique in an object other than an animal has been described for the determination of magnetic susceptibilities of oxygen in benzene or hexafluorobenzene solutions in order to estimate the amount of dissolved oxygen therein. For example, this method might be used for a remote control of oxygen content in organic solvents for oxygen pressures higher than one atmosphere. Delpuech, J. J., Hanza, M. A., and Serratrice, G.: Determination of Oxygen By a Nuclear Magnetic Resonance Method. *J. Magnetic Resonance.* 36:173–179 (1979). Finally, it has been demonstrated with NMR techniques in an object other than an animal that the solubilities of oxygen (in mole fractions) are higher in fluoroalkanes than in previously reported hexafluorobenzene. Hanza, M. A. et al.: Fluorocarbons as Oxygen Carriers. II. An NMR Study of Partially or Totally Fluorinated Alkanes and Alkenes. *J. Magnetic Resonance.* 42:227–241 (1981).

Studies directed to conformational equilibria and equilibration by NMR spectroscopy have been conducted, particularly with cyclohexane and fluorocyclohexane rings. In such applications, the position of the equilibria between conformational isomers and measurements of rates of equilibration of such isomers as a function of temperature have been determined. The studies, however, were dependent upon the implementation of known temperatures to determine the equilibria and equilibrium rates. Roberts. J. D.: Studies of Conformational Equilibria and Equilibration by Nuclear Magnetic Resonance Spectroscopy. *Chemistry in Britain.* 2:529–535 (1966); Homer, J. and Thomas, L. F.: Nuclear Magnetic Resonance Spectra of Cyclic Fluorocarbons. *Trans. Faraday Soc.* 59:2431–2443 (1963). Further, it has been illustrated that carbon-13 may be employed as a kinetic thermometer in a laboratory environment. This particular application requires the examination system to contain at least two chemically exchanging sites which correspond to one exchange process and an independent means of determining the kinetic parameters describing the exchange process in order for carbon-13 to serve as a kinetic thermometer. Such application, however, is limited to determining temperature at coalescence and, thus, is operable at only one temperature for each independent exchange process as opposed to over a continous range. Further, the method is employed as a calibration technique. Still further, its accuracy is inherently unreliable to be of practical significance. Sternhell, S.: Kinetic $^{13}$C NMR Thermometer. *Texas A&M University NMR Newsletter.* No. 285: 21–23 (June 1982).

Temperature has been measured by means of the NMR spectrum of a liquid sample for the purpose of calibrating the temperature control apparatus of an NMR spectrometer. Many features of the NMR spectrum, for instance chemical shifts, often show weak temperature dependence, and could be used to determine temperature. Bornais, Jr. and Brownstein, S.: A Low-Temperature Thermometer for $^1$H, $^{19}$F, and $^{13}$C. *J. Magnetic Resonance.* 29:207–211 (1978). In this particular reference, the peak separation and spin-spin coupling in the proton NMR spectrum of a liquid test sample changed by 1.75 Hz and 0.07 Hz, respectively, when the temperature was varied by 20.5° C. In objects, such as animals, where the best obtainable spectral resolution could be 10 to 50 Hz or larger, and it is desired to measure temperatures to an accuracy of 1° C. or 2° C. or better, such a means of temperature measurement is inapplicable.

As to temperature in an animal, it is well known that temperature provides clinicians with an excellent prognostic indicator as to the condition of the animal. For instance, an abnormal fluctuation in temperature such as an increase may reflect infection or hyperthermia, while a decrease may represent ischemia or hypothermia. Thus, it is necessary to measure temperature in an animal accurately, inexpensiveiy and reliably. Heretofore, temperature measurements have generally consisted of invasive and cumbersome techniques that often result in less than reliable measurements. For example, present techniques comprise invading needles, electrical wires, cables, or instruments that must be inserted into a region of interest. Such penetrating procedures possess unfortunately the potential to cause chemical and biological contamination to the host. Thus, proper preparation and sterilization procedures are required to prevent transmittal and corrosive contamination should the instruments to detect temperature be reused. Another disadvantage inherent to the conventional techniques concerns the discomfort and inconvenience experienced from communication with penetrating probes. Consequently, the accuracy and reliability of these conventional techniques may be adversely compromised. As to highly delicate structures, the temperature may be obtained but not without sacrifice to the integrity of the structure. Generally, the structure may be damaged, repositioned, or its dimensions changed. There is a further possibility of short circuiting the employed instruments adding additional expense and time to the procedure. Still another disadvantage involves the susceptibility of the instrument itself when exposed to physical and chemical extremes which may interfere with its reliability. Finally, conventional techniques are unable to measure a continuous temperature field in an object or animal and, thus, the invasive and cumbersome procedure must be duplicated for each time or at each point in space a temperature measurement is desired, or employ simultaneously a large number of temperature sensors.

It is apparent from the above brief overview directed to the limitations of NMR techniques and various methods for measuring temperature in an object or animal and the current state of knowledge that there is a need to provide an improved method that more effectively and advantageously detects, measures, and monitors continuously temperatures of an object or animal.

SUMMARY OF THE INVENTION

The present invention is directed to a novel method of detecting a temperature of an object utilizing nuclear magnetic resonance (NMR) techniques. Essentially, the novel method involves detecting indirectly a temperature of an object by observing detected radio-frequency signals derived from an element of a compound present in or associated with the object having at least one conformational isomer wherein the compound is influenced by the temperature, and comparing the detected signals as a means to detect the temperature of or within an object. The difference between the line position, or rate at which interconversion occurs, or the intensities of the line, i.e., spectral line, of the detected signals derived from the element of a compound having conformational isomers provides distinct parameters to detect temperature in an object. Further, temperatures in an object may be detected from the relaxation times, e.g., the spin-lattice relaxation time $T_1$ or the spin-spin relaxation time $T_2$, from the detected signals derived from the element. Other parameters that may still further be utilized to detect temperature in an object are spin-spin coupling derived from the detected signals of an element of a compound having conformational isomers, or quadrupole couplings in the case of such a compound in an environment wherein quadrupole couplings may appear in the spectrum, and if the element is examined is capable of exhibiting a quadrupole coupling.

One main advantage to the present method is that temperature may be detected in an animal. Another main advantage is that temperature may be detected non-invasively, non-destructively and continuously utilizing NMR techniques in accordance with the principles of the present invention. Still another advantage to the present method is that temperature in an object or animal may be imaged into one-, two-, or three-dimensional projections.

It has been an objective of the present invention, therefore, to provide a method of detecting at least one temperature of an object comprising subjecting said object to an NMR spectrometer, detecting radio-frequency signals derived from an element of a compound present in or associated with the object having at least one conformational isomer wherein said compound is influenced by said temperature, and comparing said detected signals as a means to detect said temperature. The difference between the detected signals for the same element, or spectral positions or chemical shifts, correspond to the temperature of the object. Further, the intensity of each detected signal which is representative of the concentration, or amount, of each conformational isomer, also corresponds to the temperature. Still further, the rate at which interconversion occurs between conformational isomers also corresponds to the temperature. Still further, the difference in spectral positions or chemical shifts, relaxation times, e.g., $T_1$ or $T_2$, spin-spin couplings or quadrupole couplings provides other means in which to determine the temperature in said object. Once spectral positions or chemical shifts, relaxation times, spin-spin couplings or quadrupole couplings have been observed for an element of a compound having conformational isomers wherein the compound has been influenced by temperature, such observed parameters may be compared to standard NMR spectral or chemical shifts, relaxation times, spin-spin couplings or quadrupole couplings determined and established for an element in the presence of varying known temperatures as a means to determine at least one temperature in an object. In effect, the temperature may be determined from the exchange rate or equilibrium constant between conformational isomers, the differences in the spectral lines, as well as changes in the relaxation times, spin-spin couplings and quadrupole couplings.

In accordance with the present invention, the element detected is, but not limited to, fluorine. When the element being detected is fluorine, a perfluorocarbon compound or any derivative thereof and more preferably a perfluorocyclocarbon compound may be introduced into the animal as a means to provide an animal sufficient detectable amounts of fluorine from a compound having conformational isomers. An example of such a perfluorocyclocarbon compound is perfluorodecalin. Aqueous artificial blood compositions which incorporate suitable perfluorocarbon compounds may be used.

In addition, the present invention is predicated in part upon further processing the detected signals, which are derived from an element of a compound present in or associated with an object having conformational isomers and influenced by temperature, to provide at least one projection (dimension) of at least one temperature of the object while also providing a high resolution two-dimensional spatial map (image). The detected signals may further be used to reconstruct one-, two-, or three-dimensional temperature images. The images may be derived from chemical shifts, relaxation times, spin-spin couplings or quadrupole couplings. Thus, the present invention provides a non-invasive, non-destructive method to generate a one-, two-, or three-dimensional thermal map for an animal in vivo. Further, similar volume NMR thermographic images may be obtained from objects other than animals according to the methods of the present invention. In practicing the present invention, the novel method may be utilized to determine and monitor continuously thermal physiological states for an animal in vivo and thermal states in an object.

It is acknowledged by the inventor herein that U.S. Pat. Nos. 4,319,190 and 4,361,807 disclose methods of imaging chemical shifts in a body. However, even though such methods to image chemical shifts were reported, it had not been previously known that such methods may be uniquely effective to image indirectly temperatures within an object or animal. Furthermore, such findings and other advantages of the present invention and the manner of their implementation as described herein are considered unexpected and unobvious and will become more apparent upon the following detailed description.

DETAILED DESCRIPTION OF THE INVENTION

In a presently preferred embodiment, practice of the novel method of this invention to detect at least one temperature of or within an object employs examination of an NMR spectrum for a detected element in an object influenced by a temperature to determine the temperature of or within the object. Such examination provides for the determination of temperature of an object from spectral positions or chemical shifts, relaxation times, e.g., $T_1$ and $T_2$, spin-spin couplings and quadrupole couplings derived from radio-frequency signals for an element of a compound having conformational isomers influenced by temperature. By conformational isomer, it is meant any one of a related set of internally rotated, bent, translated or associated arrangements or juxtapositions of parts or chemical forms of a molecule or ion of a compound, or any one of a set of related positional orientations, translations or other configurations of a molecule or ion of a compound in a crystal lattice or other similar microscopic environment, such that exchange or interconversion between said members of the set will cause exchange narrowing or other effects in an NMR spectrum as described in the detailed description of the invention. The determination of temperature of an object according to the NMR techniques and principles of this invention have not heretofore been performed. Essentially, the novel method of the present invention detects indirectly at least one temperature in an object by its effects on the spectrum, i.e., chemical shifts, relaxation times, spin-spin couplings and quadrupole couplings of a detected element. The teachings of the present invention may further be applied to animals to determine temperature within the animal.

By chemical shift, as defined in the Glossary IN: Kaufman, L., Crooks, L. E. and Margulis, A. R.: *Nuclear Magnetic Resonance Imaging in Medicine,* First Edition. New York-Tokyo: Igaku-Shoin. p 233 (1981), it refers to the shielding effect that electronic orbital motions have on the magnetic field at a nucleus. The chemical shift will therefore be proportional to the applied magnetic field and may be observed as slightly displaced peaks on a spectrum. Chemical shift can further be defined as the difference between the strength of an external magnetic field and the resulting local field of a selected element being detected. Thus, the horizontal position of the spectral line, i.e., the resonance, is determined by the chemical identity of the group in which the observed nucleus resides. For illustrative purposes, if an element in the structure of a compound is detected, and the temperature of said compound is sufficiently low such that the rate of interconversion between conformational isomers is much less than the chemical shift separation of the spectral lines of the conformational isomers measured in Hz, the position of each resonance in the spectrum for the element will correlate to a particular conformational isomer of the compound. In other words, the environment surrounding the detected element of a compound differs for each of its conformational isomers. Thus, a different horizontal position of a spectral line, which reflects a chemical shift that exists for the element being detected, can be expected for that element. When the temperature of the compound is sufficiently high such that the rate of interconversion between conformational isomers is much greater than the chemical shift separation of the spectral lines of the conformational isomers at sufficiently low temperature, the NMR spectrum of the compound at sufficiently high temperature will show only one single spectral line with spectral position of the spectral line being determined by the chemical shifts at sufficiently low temperature and the amount of each conformational isomer present at sufficiently high temperature. As the temperature of the compound is varied continuously between high and low temperatures, the NMR spectrum will display corresponding continuous changes between high and low temperature limiting spectral forms. This effect is known as exchange averaging or exchange narrowing. The advantage of the present invention over previous methods of measuring temperature by NMR is that because the rate of interconversion between conformational isomers can be a very strong function of temperature, the spectral change produced by changing the temperature of a compound exhibiting exchange narrowing can be very much greater than the spectral changes which occur when exchange narrowing is not taking place. Whereas spectral changes wich do not involve exchange narrowing are inapplicable for measuring temperature in an object or animal, where the spectral resolution is much poorer than in typical chemical test samples, spectral changes which exhibit exchange narrowing can be used to measure temperature to a high degree or accuracy in the object or animal. Other spectral features, e.g., spin-spin couplings, quadrupole couplings and relaxation times, will display similar behavior when a compound undergoes exchange narrowing, and can similarly be used to detect temperature. Therefore, it is to be understood according to the principles of the present invention, that since the interconversion between the conformational isomer forms of a compound will characterize the temperature, the spectrum will correspond to the temperature in an object.

Further, since the relative amounts of each of the conformational isomers will correlate with the temperature, the relative intensities of the spectral lines of each conformational isomer at a temperature sufficiently low such that exchange narrowing has not occurred will characterize the temperature. Further, since the spectral position of a compound with conformational isomers at a temperature sufficiently high such that exchange narrowing has occurred will correlate with the relative amounts of each conformational isomer, the spectral position of the compound will characterize the temperature. These two effects will have strong and useful temperature dependences when the thermodynamic Gibbs free energy difference $\Delta G$ between the conformational isomers divided by the universal gas constant R is comparable in magnitude to the absolute temperature T.

Once the spectra, e.g., chemical shifts, have been observed for a detected element of a compound having at least one conformational isomer, the temperature of the object associated with the compound may be, but not exclusively, determined from (1) the spectral lines as a measure of the rate at which isomeric interconversion or exchange occurs, (2) the spectral line intensities, i.e., amount, of each isomer and (3) the distance between the horizontally positioned spectral lines for each isomer as a direct reflection of temperature, as determined from the spectrum. Notwithstanding temperature dependence as to all three parameters, the determination of temperature from all three methods are derived from the principle that a compound having at least one conformational isomer interconverts uniquely at different temperatures. Because conformational isomers interconvert, the rate at which the isomeric interconversion occurs, the distance between the spectral lines for each isomer, as well as the intensity, or amount of each isomer are all temperature dependent. Therefore, it is to be understood according to the principles of the present invention, that since the shielding influence derived from the environment surrounding an element of conformational isomers differs, and that since the rate of exchange between conformational isomers corresponds to a temperature in an object, then the distance between the horizontal position of spectral lines as well as the relative intensities of spectral lines, or amounts, of each isomer form will also correspond to the temperature. Thus, the determination of the spectra or chemical shift for an element of a compound having conformational isomers provides at least three methods to determined temperature in an object or animal therefrom.

Accordingly, to determine the temperature in an object or an animal, a mathematical computation measuring the rate of exchange between isomers, the intensities, or amount, of isomers, and the distance between horizontal line positions for each isomer, which are all representative of the temperature, may be performed. When temperature is determined by the rate of exchange between isomers, the rate for exchange k, or the number of interconversions per second, must be compared with the chemical shift difference δ in Hz, as opposed to ppm (parts per million). When k is much greater than δ, only a single line is observed positioned horizontally at the concentration-weighted average shift value. When k is much less than δ, independent lines are observed positioned horizontally at the respective values for each conformational isomer. Hence, the rate of exchange or interconversion is in direct relationship to the spectrum which is a reflection of temperature. Starting at low exchange rates or low temperatures and increasing the rates with high temperatures, the independent spectral lines will move toward each other, broaden, and coalesce to finally form a single sharp line at a high rate of exchange. An example of a mathematical computation to determine k utilizing the teachings of the present invention concerns the slow exchange side of coalescence. Thus, the line separation may be determined, for example, by the following formula:

$$\frac{\delta}{\delta_0} = \sqrt{1 - \frac{k^2}{2\pi^2 \delta_0^2}}$$

wherein δ equals line separation in Hz and $\delta_0$ equals line separation in Hz at low rate limits. The formula above is for illustrative purposes and is applicable for certain limited situations which are satisfied in accordance with the principles of this invention. Thus, if δ is determined for a compound in an object by NMR techniques in accordance with this invention, and $\delta_0$ is known for the compound, the rate of exchange k for the compound may be determined. Once determined, the rate of exchange k for the compound may, for example, be compared to predetermined exchange rates for that particular compound corresponding to known temperatures, or the NMR equipment may be calibrated to known temperatures corresponding to the rate of exchange k to detect the temperature in an object. Ideally, it is an object of the present invention to detect elements of compounds that are on the slow exchange side but approaching coalescence when small changes in temperature are to be determined. Further, when temperatures in an animal are determined, it is preferred for compounds to be in the slow exchange rate at physiological temperatures. In other words, such compounds should generally be "high-sensitivity" compounds wherein easily discernable, well-resolved spectral shifts are usually observed when there are relatively small changes in temperature.

If temperature is to be determined from spectral line intensities derived from a spectrum, a mathematical computation may also be performed. The total area under the spectral line, or the integral of the line, is proportional to the number of nuclei of a particular isomer being detected. Thus, the intensity of each spectral line corresponds to an amount of each isomer of a compound in a particular form which exists at a particular temperature. Like rate of exchange, therefore, the intensity of spectral lines and more particularly the average intensity of spectral lines is representative of temperature which is uniquely characteristic for each compound. An example of the mathematical computation that may be used according to the teachings of the present invention, which is similar to the one for rate of exchange, determines the equilibrium constant K, or ratio, between conformational isomers, and is demonstrated by $$\text{equilibrium constant } K = \frac{C_B}{C_A} = \frac{\text{intensity of line } B}{\text{intensity of line } A \text{ (measured from spectrum)}}$$

wherein $C_A$ and $C_B$ are the concentrations of the isomers in form A and B, respectively. The concentrations of each isomer may of course be obtained from the intensities of the spectral lines detected from an element which is representative of temperature. The employment of this technique, i.e., measurement of line intensities, to determine temperature in an object provides a sensitivity similar to the technique utilized for the rate of exchange method. Further, as with the rate of exchange method, the equilibrium constant K, or ratio, method is uniquely characteristic for a particular compound at a particular temperature. Still further, compounds in the slow exchange limit or high-sensitivity compounds, are generally preferred particularly at physiological temperatures. It is worth noting, however, that the line intensities may be altered by changing various settings on the instrument, and will be affected by experimental conditions such as pulsing rate and sample characteristic such as relaxation times associated with the spectral line under consideration. Thus, measurement of temperature by the rate of exchange method is likely to be more accurate and therefore is the preferred method.

If so desired, a further computation may be made once the equilibrium constant K, or ratio, is established to determine the enthalpy difference ΔH between the existing isomers demonstrated by $$\frac{dK/K}{dT} = \frac{d\ln K}{dT} = \frac{\Delta H}{RT^2}$$

wherein ΔH corresponds to a compound having two conformational isomers at a particular temperature.

As to the spectral line position method, once a spectrum has been obtained for a detected element of a compound having conformational isomers, the difference in the horizontal line positions for each isomer is representative of the temperature. Thus, as the temperature changes, the horizontal line positions are altered for isomers of a compound uniquely characterizing temperature. It is to be understood, however, that the line positioning method is a reflection of the rate of isomer exchange.

The employment of spin-spin coupling to measure temperature involves the effect which splits a resonance into a group of spectral lines. This phenomenon results from other magnetized nuclei within the molecule. In effect, these internal magnetized nuclei will align in a small number of discrete ways with the applied strong magnetic field of the instrument, and thereby produce at the nucleus being observed several discrete, closely spaced values of magnetic field as opposed to a single value. Thus, perturbations are observed in the spectral lines. The number of perturbations depends on the number of nuclei of a given type causing the splitting and their characteristics. The space in between the lines, i.e., the size of the couplings, depends on the characteristics of the nucleus under observation, the nuclei causing the splitting and the characteristics of the electrons in the molecule. Further, the effect is dependent on the types and numbers of bonds between the interacting nuclei. For example, when a pair of spaced lines, or doublet, is observed, as opposed to a single peak, the spectral line has been split into two. To determine the temperature, similar techniques as employed with chemical shifts are utilized, for example, wherein the averaging effect on the couplings or the difference in the position of the couplings are measured. Such techniques, like those determined from chemical shift, are derived from the principle that a compound having at least one conformational isomer interconverts uniquely at different temperatures. This procedure, however, may be more difficult to implement as a means to measure temperature accurately and therefore the employment of the rate of exchange method described above is to be preferred.

Temperature may also be determined by relaxation times. The two most common relaxation times are denoted $T_1$, or spin-lattice relaxation time, and $T_2$, or spin-spin relaxation time. Each resonance of an element of a compound having conformational isomers has its own specific values of these relaxation times, although the individual components of a multiplet, or a spin-spin coupling effect, tend to be nearly identical in relaxation properties. Relaxation rates are the reciprocals of relaxation times. $T_1$ is the measure of the rate at which the nuclei become aligned with the instrumental magnetic field or the rate at which the nuclear spins re-establish thermal equilibrium (this is not related to thermal or equilibrium for the compound). Specifically, the magnetization M of the nuclei normally approach the ultimate or equilibrium value exponentially. $T_1$ is then the time constant of the exponential demonstrated by $$[M(t) - M(t = 0)] = e^{-t/T_1}$$
$$M \text{ at time } t \quad \text{ultimate } M$$

Experimentally, $T_1$ determines the rate the nuclei can absorb or emit energy. In a continuous wave procedure, it determines the maximum radio-frequency power that may be used without the signal disappearing due to saturation. In a pulsed or FT (Fourier transform) experiment, it determines the maximum rate at which pulses may be applied.

$T_2$ is a measure of the width of a resonance line in a spectrum, and only has meaning in the context of a particular line shape. For example, if a line has a Lorentzian shape: functional form of $$y = \frac{1}{1 + x^2} \text{ then } T_2 = \frac{1}{\pi(\text{width of line at half maximum height})}$$

If the line has a different shape, however, a different definition must be used. Experimentally, $1/T_2$ is a measure of the width of a line. In a pulsed experiment, $T_2$ is a measure of the time it takes for the free induction decay (FID) to die away. Once again, if the line is Lorentzian in shape the FID envelope is exponential and $T_2$ is the time constant.

In practice, the NMR spectrum may be obtained by applying RF pulses, i.e., 90° or shorter pulses as desired to optimize sensitivity to obtain FIDs, acquiring and signal averaging these signals and Fourier transforming them to obtain the spectrum. $T_1$ may be measured by inversion recovery: 180° pulse, delay time, 90° pulse acquire FID. The signal amplitude may be fitted to an experimental function of the delay time to obtain $T_1$. $T_2$ may be measured by a spin-echo technique: 90° pulse, delay, 180° pulse, same delay, acquire signal. Signal amplitude is fitted to an exponential function of delay time to obtain $T_2$. Many variations of these procedures have been published and can be employed herein in accordance with the principles of this invention. If temperature is to be determined from relaxation times, a difference in for example $T_1$, the rate in which the nuclei re-align or re-establish thermal equilibrium, or $T_2$, the rate of decay of the FID, may be measured as a function of temperature. The method described may further be reconstructed to image temperature in an object. Thus, changes in the relaxation times, are uniquely characteristic for determining temperature from a compound over applicable temperature ranges.

Accordingly, the broadest aspect of the invention is to provide a novel and improved method of detecting indirectly at least one temperature of an object utilizing NMR techniques. More specifically, the method involves the obtainment of an NMR spectrum to determine chemical shift, relaxation times, spin-spin couplings and quadrupole couplings for a detected element of a compound having conformational isomers in the object influenced by at least one temperature of an object to determine said temperature. In another broad embodiment, this invention, according to its princples and the teachings, may be employed to detect temperature of an animal. In still another broad embodiment, the invention may determine temperature from the rate of exchange k, the equilibrium constant K, the difference in the horizontal positioning of the spectral lines, differences in the relaxation times, e.g., $T_1$ and $T_2$, differences in the spin-spin coupling, and differences in quadrupole couplings. In still another broad embodiment, the invention may image from chemical shift, relaxation times such as $T_1$ or $T_2$, spin-spin couplings or quadrupole couplings at least one temperature of an object or animal as a means to determine and monitor thermal states of an object or to determine or monitor thermal physiological states of an animal. In still another broad embodiment, the invention may be employed to determine and image temperature in a solid, as defined herein, or liquid. The inventive method is unique because it is non-invasive, non-destructive, and non-ionizing to an object or animal. Further, it may be employed continuously to obtain the above-mentioned determinations or results. The novel method of detecting at least one temperature of an object according to the principles of my invention comprises subjecting said object to a NMR spectrometer, detecting radio-frequency signals in a spectral pattern derived from an element of a compound having at least one conformational isomer wherein the compound is influenced by the temperature, and comparing the signals to detect at least one temperature. The detected signals for the element correspond to spectral positions or chemical shifts representative of the conformational isomers of the compound. As to chemical shifts or spectral positions, the difference between the spectral positions may correspond to a chemical exchange rate k between the conformational isomers representative of the temperature. Further, the difference between the spectral positions is in itself representative of said temperature. Still further, the intensities of the spectral lines are also representative of said temperature under appropriate conditions. Because the shielding influences differ in each isomeric form, different signals are detected corresponding to the spectral positions or chemical shift for a detected element. Therefore, the rate of exchange k, the equilibrium constant K, the difference in the horizontal line positioning as well as differences in relaxation times, quadrupole couplings and spin-spin couplings may be interpreted to correspond to at least one temperature of an object. The most preferred method for detecting temperature according to the principles of the present invention is the rate of exchange k method.

It will be understood that different spectra are obtained for emitted radio waves by the detected elements of a compound in the presence of a temperature and such spectra may be contrasted with those obtained at known reference temperatures. Thus, the differing spectra provide a means of detection or measurement of the temperature which is influencing the spectrum of the detectable nuclei. The determination of chemical shift, relaxation times, spin-spin couplings and quadrupole couplings provide parameters representative of the temperature. For instance, the determined exchange rate k, the equilibrium constant K, and the differences in horizontal line position, as well as relaxation times, spin-spin couplings, and quadrupole couplings may be compared to standard exchange rates k, equilibrium constants K, and horizontal line positions, relaxation times, spin-spin couplings and quadrupole couplings, respectively, determined and established for an element of a compound influenced by variable known temperatures independent of an object as a means to determine the temperature. It should be indicated, however, that when a calibration method is employed, the signals detected for an element of a compound independent of an object will preferably be influenced by known temperatures and in an environment similar to that in the object to determine and establish standard rates of exchange k, equilibrium constants K, differences in horizontal line positions, relaxation times, spin-spin couplings and quadrupole couplings for the element of the compound. In an alternative technique, the NMR equipment may be calibrated so that temperature may be directly determined from the computed parameters cited herein.

Further, thermal maps in an object or animal in vivo may be obtained in one-, two-, or three-dimensional images from chemical shift, relaxation times, e.g., $T_1$ or $T_2$ derived from, for example, inversion recovery for $T_1$ and spin-echo for $T_2$, spin-spin couplings and quadrupole couplings. The determination and imaging of inanimate as well as animate solids and liquids may also be conducted according to the principles of the present invention. By the word solid, it refers to solids and semisolids such as gels and biological solids, for example, such as in plants, tissues, etc.

In another aspect in accordance with the present invention, the presently preferred element to detect in an object or animal as a means to indirectly detect temperature is fluorine. As stated in the background, fluorine is uniquely suited for NMR techniques because it has a spin ½, giving relatively uncomplicated and well-resolved narrow spectral lines, 100 percent natural isotopic abundance, large chemical shifts, a magnetogyric constant similar to protons so that the same equipment may be used and relatively low natural biological occurrence in a form observable by normal NMR techniques. In order to follow the teachings of this invention, one must introduce into an object or animal a compound containing a sufficient amount of fluorine so that fluorine may be detected by NMR techniques. By introduce, it refers herein, as to the administration of a compound by inhalation, injection, oral introduction or other appropriate means. Further, such fluorine compounds must be chemically compatible with the object or animal, physically compatible for formulation of a composition that may be suitably introduced into the object, and provide unambiguous, easily discernible NMR signals so that chemical or spectral shift can be accurately determined. It has been found that perfluorocarbons and any derivatives thereof are ideally suited for application according to the principles of the present invention. With respect to the compounds disclosed herein, they are relatively incompatible with their surrounding environments in the sense that they do not mix or react with their surrounding environments, and, thus, will provide chemical shifts that correspond reliably to temperature. Another advantage to these compounds is that they should provide unambiguous, easily discernible signals enabling chemical shifts derived from the isomers of these compounds which are influenced by at least one temperature in an object or animal to be readily determined. The preferred perfluorocarbons or any derivatives thereof that may be used according to the teachings of this invention are perfluorocyclocarbons or emulsions thereof such as those employed in artificial bloods. Nevertheless, any perfluorocarbon or derivative thereof may be used in this present invention that demonstrates RES-phobic properties as is defined in U.S. Pat. Nos. 3,911,138 and 4,105,798. Such compounds include perfluoro (methylcyclohexane), perfluoro-1-methyldecalin [also known as perflouro (decahydro-α-methylnaphthalene)], perfluoro (1,3-dimethylcyclohexane), perfluoro (decahydronaphthalene), and perfluoro (decahydrodimethylnaphthalene), or mixtures thereof, perfluorinated bicyclononane, perfluorinated bicyclooctane, perfluorinated adamantane, perfluoromethyladamantane and perfluorodimethylbicyclo [3.3.1.]nonane, perfluorodimethyladamantane and perfluorotrimethylbicyclo[3.3.1.]nonane, perfluorotetrahydrodicyclopentadiene, perfluorinated bicyclononane, perfluorinated bicyclooctane, perfluorinated adamantane, perfluoromethyladamantane and perfluorodimethylbicyclo[3.3.1]nonane, perfluorodimethyladamantane and perfluorotrimethylbicyclo[3.3.1.]nonane, and perfluorotetrahydrodicyclopentadiene and perfluorobicyclo[5.3.1] decane, and perfluorotributylamine (FC47), perfluorodecalin (PP5), perfluorotetrahydrofuran (FC80), perfluoroether (PID) [$(CF_3)_2CFOCF_2(CF_2)_2$ $CF_2OCF(CF_3)_2$], perfluoroether (PIID) [$(CF_3)_2CFOCF_2(CF_2)_6CF_2OCF(CF_3)_2$],

perfluoropolymer (E3) [$CF_3CHF(OCF_2CF)_2OCF_2CF_2CF_3$], perfluoropolymer (E4) [$CF_3CHF(OCF_2CF)_3OCF_2CF_2CF_3$], perfluoroetherpolyer (Fomblin Y01), perfluorododecane, perfluorobicyclo[4.3.0]nonane, perfluorotrimethylcyclohexane, perfluoroisopropylcyclohexane, perfluoroendotetrahydrodicylopentadiene, perfluorobicyclo]5.3.0.]decane, perfluorotetramethylcyclohexane, perfluoro-1-methyl-4-isopropylcyclohexane, perfluoro-n-butylcyclohexane, perfluorodimethylbicyclo[3.3.1.]nonane, perfluoro-1-methyl adamantane, perfluoro-1-methyl-4-t-butylcyclohexane, perfluorodecahydroacenaphthlene, perfluorotrimethylbicyclo[3.3.1.]nonane, perfluoro-n-undecane, perfluorotetradecahydrophenanthrene, perfluoro-1,3,5,7- tetramethyladamantane, perfluorododecahydrofluorene, perfluoro-1,3-dimethyl adamantane, perfluoro-n-octylcyclohexane, perfluoro-7-methyl bicyclo[4.3.0.]nonane, perfluoro-p-diisopropylcyclohexane, and perfluoro-m-diisopropylcyclohexane, and perfluorocyclocarbons such as perfluoro (methylcyclohexane), perfluoro (1,3-dimethylcyclohexane), perfluoro (decahydronaphthalene), perfluoro (decahydro-1-methylnaphthalene) and perfluoro (decahydrodimethylnaphthalene), or mixtures thereof, perfluorinated bicyclononane, perfluorinated bicyclooctane, perfluorinated adamantane hydrocarbon, perfluoromethyladamantane and perfluorodimethylbicyclo[3.3.1.]nonane, perfluorodimethyladamantane and perfluorotrimethylbicyclo[3.3.1.]nonane, perfluorotetrahydrodicyclopentadiene and perfluorobicyclo[5.3.0.]decane, perfluorotetrahydrodicyclopentadiene, perfluorinated bicyclononane, perfluorinated bicyclooctane, perfluorinated adamantane, perfluoromethyladamantane and perfluorotrimethylbicyclo[3.3.1.]nonane, and perfluorotetrahydrodicyclopentadiene and perfluorobicyclo[5.3.0] decane.

In accordance with this description and presently preferred embodiment, it will become apparent that elements other than fluorine may be selected to detect at least one temperature of an object. For example, based upon sensitivity and sufficiency requirements for present NMR techniques, other elements with these properties, specifically, aluminum-27, boron-11, carbon-13, chlorine-35, chlorine-37, deuterium, magnesium-25, nitrogen-14, nitrogen-15, oxygen-17, phosphorus-31, platinum-195, proton, silicon-29, and sodium-23, and other similar elements may be employed.

In another aspect of the present invention, a single temperature or several temperatures may be detected in an object or animal. Thus, the present invention may be used to determine temperature fluctuations and distributions. In another aspect of the present invention, due to the advantageous non-invasive, non-ionizing and non-destructive properties of NMR techniques, the novel method of this invention may be employed continuously. Further, the magnetic field to be employed with the method of the present invention may be generated by iron-core, resistive air-core, and super conducting air-core magnet designs. According to the principles of this invention, low and high resolution NMR may be employed. Of course, as the resolution increases the spectra will become better resolved and defined for a detected element. Thus, whenever possible, high resolution NMR will be employed to detect an element of a compound. Upon examination, spectral superimposition or overlapping is undesirable according to the teachings of the present invention and usually will not be observed when fluorine, for example, is being detected. Still further, the method of this invention may be used to determine and monitor a thermal physiological state in an animal and determine and monitor a thermal state in an object. A basic advantage of such an application provides medical and biological communities with a reliable analytical tool for diagnostic purposes in an animal. Another advantageous embodiment of the present method is that it may be used to detect signals for an element influenced by a temperature in at least one region in an animal or object which corresponds to the distribution of temperature in the animal or object. Thus, physiologic temperatures or temperature states in various regions of an animal or object, respectively, may be determined.

In another aspect of the present invention, an indirectly detected temperature may be uniquely and advantageously imaged into one-, two- or three-dimensional projections reconstructed from chemical shift, relaxation times, e.g., inversion recovery $T_1$, or spin-echo $T_2$, or spin-spin couplings derived from a detected element of a compound influenced by at least one temperature in one or more regions in an object. This objective may be accomplished in accordance with certain principles of this invention by spatially defining detected elements in an object influenced by at least one temperature. For instance, the detected signals in an object may be for at least one region or a plurality of individual parts along at least one region in an object. Further, the region may constitute a strip and signals may be detected for a plurality of individual parts, each along at least one strip in an object. Still further, the region may represent at least one substantially planar slice or a series of parallel planar slices in an object. If spatial distribution is desired within at least one slice, signals may be detected for at least one strip or a plurality of strips perpendicular to the slice. To further define the spatial distribution of an element influenced by temperature in an object, signals may be detected for at least one part, each along at least one of the strips and at least one of the slices. Still further, the region may also constitute a matrix at least in an area of interest in said object. The methods to define spatial resolution are well known wherein one or more magnetic gradients may be employed to discriminate areas in which similar elements are located. Any of the teachings to obtain spatial distribution of an element influenced by temperature may be employed with the principles of the present invention so long as they do not depart from its spirit. Examples of obtaining spatial distribution are disclosed, for example, in U.S. Pat. Nos. 4,297,637, 4,318,043 and 4,361,807. Once spatial distribution of an element influenced by a temperature has been observed, NMR projections may be reconstructed from chemical shift, relaxation times, spin-spin couplings and quadrupole couplings of the element. Such methods may include zeugmatography, NMR tomography, surface coil technicques and chemical microscopy as disclosed in Hall, L. D. and Sukumar, S.: Chemical Microscopy using a High-Resolution NMR Spectrometer. A Combination of Tomography/Spectroscopy Using Either $^1H$ or $^{13}C$. 50:161-164 (1982). Of such methods, those taught in Lauterbur et al: Zeugmatographic High Resolution Nuclear Magnetic Resonance Spectroscopy Images of Chemical Inhomogeneity within Macroscropic Objects. *J. American Chemical Society*. 97(23):6866-6868, Nov. 12, 1975, Brown in U.S. Pat. No. 4,319,190 and Burl et al in U.S. Pat. No. 4,361,807 are preferred with respect to imaging from chemical shift reconstruction, and more preferably those taught by Lauterbur and Brown. However, any imaging techniques, such as imaging from projections, FONAR, sensitive point imaging, Fourier imaging, and imaging by selective irradiation, that are compatible with the methods taught by this invention may be employed. As already cited, temperatures in an object or animal may further be imaged by such applicable techniques from the relaxation times, preferably inversion recovery from $T_1$ or spin-echo from $T_2$, spin-spin couplings and quadrupole couplings observed from the detected element influenced by a temperature within an object. In a further aspect of the present invention, temperatures may be determined and imaged in inanimate or animate solids or liquids in accordance with the teachings herein.

EXAMPLE

A small amount of 1,1,2,2-tetrafluorocyclohexane is introduced into an NMR imaging spectrometer operating with a field strength of approximately 7500 gauss. The temperature is varied in 0.5° C. increments at about −20° C., taking fluorine-19 NMR spectra at each temperature, and recording from each spectrum the value of the chemical shift difference in Hz between the spectral lines corresponding to the axial and equitorial conformer positions of the fluorines in the compound to formulate a calibration table of chemical shifts and corresponding temperatures. This compound possesses an activation energy of about 8.0 kcal mol$^{-1}$ for this interconversion as disclosed in Roberts, J. D.: Studies of Conformational Equilibria and Equilibration by Nuclear Magnetic Resonance Spectroscopy. Chem. Britain 2:529–535, (1966). Under these conditions, the maximum spectral separation is about 500 Hz. In the vicinity of about −20° C., the separation changes by about 50 Hz/° C.

Subsequently, the compound is introduced into an object wherein the temperature will be mapped. The fluorine chemical shift image of the object is obtained according to Brown in U.S. Pat. No. 4,319,190. An automated computer procedure is employed to calculate the value of temperature in each volume element of the image by measuring the spectral separation in the NMR spectrum for each volume element and deriving a temperature by interpolation from the calibration table.

This method involves no additional measurement time over that of the chemical shift imaging procedure. The computer processing time required to derive temperature is small compared to the image reconstruction time for two dimensions, and is essentially insignificant in the cse of three dimensions.

Another method would be to match the lineshape to a calibration lineshape, although this would require substantially more computer processing time. It would be practical if temperature at only a small number of points were to be determined.

In view of the above detailed descriptions and preferred embodiments, the present invention may, of course, be carried out in other specific ways than those herein set forth without departing from the spirit and essential characteristics of the invention. The present embodiments are, therefore, to be considered in all respects as illustrative and not restrictive and all changes coming within the meaning and equivalency range of the appended claims are intended to be embraced therein.

What is claimed is:

1. A method of determining temperature of an object comprising
    subjecting the object comprising a compound to an NMR spectrometer, the compound having at least two forms which are conformational isomers undergoing an exchange process between the conformational isomers which is influenced by temperature,
    exposing the compound to temperature to influence the exchange process, and
    detecting and processing radio-frequency signals derived from the nuclear magnetic resonance of an element of the compound undergoing the influenced exchange process as a determination of the temperature.

2. A method according to claim 1 wherein said object is an animal.

3. A method according to claim 1 wherein said object is a solid.

4. A method according to claim 1 wherein said object is a liquid.

5. A method according to claim 1 wherein said detected signals for said element correspond to spectral patterns representative of said conformational isomers of said compound.

6. A method according to claim 5 wherein said spectral patterns are compared to standard spectral patterns determined and established for said element influenced by varying known temperatures independent of said object as a means to determine temperature in said object.

7. A method according to claim 5 wherein difference between said spectral patterns correspond to a chemical exchange rate between said conformational isomers representative of said temperature.

8. A method according to claim 5 wherein difference between said spectral patterns is representative of said temperature.

9. A method according to claim 5 wherein relative intensities of NMR lines within said spectral patterns are representative of said temperature.

10. A method according to claim 1 wherein said temperature is determined from relaxation times derived from said detected element of said compound.

11. A method according to claim 10 wherein said relaxation times are compared to standard relaxation times determined and established for said element influenced by varying known temperatures independent of said object as a means to determine temperature in said object.

12. A method according to claim 10 wherein said relaxation times are spin-lattice relaxation times.

13. A method according to claim 1 wherein said temperature is determined from spin-spin couplings derived from detected element of said compound.

14. A method according to claim 13 wherein said spin-spin couplings are compared to standard spin-spin couplings determined and established for said element influenced by varying known temperatures independent of said object as a means to determine temperature in said object.

15. A method according to claim 1 wherein said temperature is determined from quadrupole couplings derived from detected element of said compound.

16. A method according to claim 15 wherein said quadrupole couplings are compared to standard quadrupole couplings determined and established for said element influenced by varying known temperatures independent of said object as a means to determine temperature in said object.

17. A method according to claim 1 wherein said detected element is fluorine.

18. A method according to claim 17 wherein said fluorine is derived from a perfluorocarbon or derivative thereof.

19. A method according to claim 18 wherein said perfluorocarbon or derivative thereof is introduced into said object.

20. A method according to claim 18 wherein said perfluorocarbon or derivative thereof is introduced into said animal.

21. A method according to claim 18 wherein said perfluorocarbon or derivative thereof is RES-phobic.

22. A method according to claim 18 wherein said perfluorocarbon or derivative thereof is in aqueous form.

23. A method according to claim 18 wherein said perfluorocarbon or derivative thereof is selected from the group consisting of perfluoro (methylcyclohexane), perfluoro-1-methyldecalin [also known as perfluoro(-decahydro-α-methylnapthalene)], perfluoro (1,3-dimethylcyclohexane), perfluoro (decahydronaphthalene), and perfluoro (decahydrodimethylnaphthalene), or mixtures thereof, perfluorinated bicyclononane, perfluorinated bicyclooctane, perfluorinated adamantane, perfluoromethyladamantane and perfluorodimethylbicyclo [3.3.1.]nonane, perfluorodimethyladamantane and perfluorotrimethylbicyclo[3.3.1.]nonane, perfluorotetrahydrodicyclopentadiene, perfluorinated bicyclononane, perfluorinated bicyclooctane, perfluorinated adamantane hydrocarbon, perfluoromethyladamantane and perfluorodimethylbicyclo[3.3.1]nonane, perfluorodimethyladamantane and perfluorotrimethylbicyclo[3.3.1.]nonane, and perfluorotetrahydrodicyclopentadiene and perfluorobicyclo[5.3.1]decane, and perfluorotributylamine (FC47), perfluorodecalin (PP5), perfluorotetrahydrofuran (FC80), perfluoroether (PID) [(CF$_3$)$_2$CFOCF$_2$(CF$_2$)$_2$CF$_2$OCF(CF$_3$)$_2$], perfluoroether (PIID) [(CF$_3$)$_2$CFOCF$_2$(CF$_2$)$_6$CF$_2$OCF(CF$_3$)$_2$],

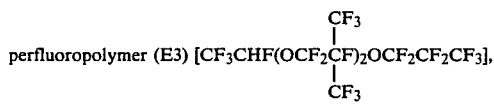

perfluoropolymer (E4) [CF$_3$CHF(OCF$_2$CF)$_3$OCF$_2$CF$_2$CF$_3$], perfluoroetherpolyer (Fomblin Y01), perfluorododecane, perfluorobicyclo[4.3.0]nonane, perfluorotrimethylcyclohexane, perfluoroisopropylcyclohexane, perfluoroendotetrahydrodicylopentadiene, perfluorobicyclo]5.3.0.]decane, perfluorotetramethylcyclohexane, perfluoro-1-methyl-4-isopropylcyclohexane, perfluoro-n-butylcyclohexane, perfluorodimethylbicyclo[3.3.1.]nonane, perfluoro-1-methyl adamantane, perfluoro-1-methyl-4-t-butylcyclohexane, perfluorodecahydroacenaphthlene, perfluorotrimethylbicyclo[3.3.1.]nonane, perfluoro-n-undecane, perfluorotetradecahydrophenanthrene, perfluoro-1,3,5,7-tetramethyladamantane, perfluorododecahydrofluorene, perfluoro-1,3-dimethyl adamantane, perfluoro-n-octylcyclohexane, perfluoro-7-methylbicyclo[4.3.0.]nonane, perfluoro-p-diisopropylcyclohexane, and perfluoro-m-diisopropylcyclohexane, and perfluorocyclocarbons such as perfluoro (methylcyclohexane), perfluoro (1,3-dimethylcyclohexane), perfluoro (decahydronaphthalene), perfluoro (decahydro-1-methylnaphthalene) and perfluoro (decahydrodimethylnaphthalene), or mixtures thereof, perfluorinated bicyclononane, perfluorinated bicyclooctane, perfluorinated adamantane hydrocarbon, perfluoromethyladamantane and perfluorodimethylbicyclo[3.3.1.]nonane, perfluorodimethyladamantane and perfluorotrimethylbicyclo[3.3.1.]nonane, perfluorotetrahydrodicyclopentadiene and perfluorobicyclo[5.3.0.]decane, perfluorotetrahydrodicyclopentadiene, perfluorinated bicyclononane, perfluorinated bicyclooctane, perfluorinated adamantane, perfluoromethyladamantane and perfluorotrimethylbicyclo[3.3.1.]nonane, and perfluorotetrahydrodicyclopentadiene and perfluorobicyclo[5.3.0]decane.

24. A method according to claim 1 wherein said element is selected from the group consisting of aluminum, boron, carbon, chlorine, magnesium, nitrogen, oxygen, phosphorus, platinum, hydrogen, silicon or sodium.

25. A method according to claim 1 wherein said temperature is detected in tissue.

26. A method according to claim 1 wherein said temperature is detected in blood.

27. A method according to claim 1 wherein said temperature is detected continuously.

28. A method according to claim 1 wherein said detected signals for said element in said object influenced by a temperature are determined for at least one region in said object.

29. A method according to claim 28 wherein at least one determined said region is a strip in said object.

30. A method according to claim 28 wherein at least one determined said region is substantially a planar slice in said object.

31. A method according to claim 30 wherein said slices are parallel in said animal.

32. A method according to claim 28 wherein at least one said region is a matrix at least in an area of interest in said object.

33. A method according to claim 28 wherein said detected signals for an element in said object influenced by a temperature in at least one said region corresponds to the distribution of said temperature in said object.

34. A method according to claim 28 wherein said detected signals for an element in said object influenced by a temperature in at least one said region is further processed to reconstruct at least one projection of said temperature in said object.

35. A method according to claim 34 wherein the detected signals are processed into a one-, two-, or three-dimensional image.

36. A method according to claim 35 wherein said image of said temperature is processed from chemical shift, spin-lattice relaxation time, spin-spin relaxation time, spin-spin coupling or quadrupole coupling.

37. A method according to claim 1 wherein said method is used to determine a thermal physiological state in an animal.

38. A method according to claim 1 wherein said method is used to monitor a thermal physiological state in an animal.

39. A method according to claim 1 wherein said method is used to monitor a thermal state in an object.

40. A method according to claim 10 wherein said relaxation times are spin-spin relaxation times.

41. A method according to claim 1 wherein the spectral pattern is representative of the temperature of the object.

42. A method for determining temperature in an area of interest in an animal comprising
introducing into the animal a perfluorocarbon or derivative thereof for providing fluorine into the area of interest, the perfluorocarbon or derivative thereof having at least two forms which are conformational isomers undergoing an exchange process between the conformational isomers which is influenced by temperature in the area of interest,
subjecting the animal to an NMR spectrometer,
exposing the perfluorocarbon or derivative thereof to temperature to influence the exchange process, and detecting and processing radio-frequency signals from the nuclear magnetic resonance of the fluorine of the perfluorocarbon or derivative thereof undergoing the temperature influenced exchange process as a determination of the temperature in the area of interest.

43. A method according to claim 42 wherein the perfluorocarbon or derivative thereof is in an aqueous medium.

44. A method of claim 42 wherein the perfluorocarbon or derivative thereof is a perfluorocyclocarbon.

45. A method of claim 42 wherein the temperature is determined from relaxation times, spin-spin couplings or chemical shifts.

46. A method of claim 45 wherein the relaxation times are spin-lattice relaxation times.

47. A method of claim 45 wherein the relaxation times are spin-spin relaxation times.

48. A method of claim 42 wherein said detected signals are further processed into a one-, two-, or three-dimensional image.

49. A method of detecting at least one temperature in an object comprising subjecting said object to an NMR spectrometer, detecting radio-frequency signals in a spectral pattern of a fluorine element derived from a perfluorocarbon or derivative thereof having at least one conformational isomer associated with said object wherein said fluorine element is influenced by said temperature, and comparing said detected signals as a means to detect said temperature.

50. A method according to claim 49 wherein said perfluorocarbon or derivative thereof is introduced into said object.

51. A method according to claim 49 wherein said perfluorocarbon or derivative thereof is introduced into said animal.

52. A method according to claim 49 wherein said perfluorocarbon or derivative thereof is RES-phobic.

53. A method according to claim 49 wherein said perfluorocarbon or derivative thereof is in aqueous form.

54. A method according to claim 49 wherein said perfluorocarbon or derivative thereof is selected from the group consisting of perfluoro (methylcyclohexane), perfluoro-1-methyldecalin [also known as perfluoro(-decahydro-α-methylnapthalene)], perfluoro (1,3-dimethylcyclohexane), perfluoro (decahydronaphthalene), and perfluoro (decahydrodimethylnaphthalene), or mixtures thereof, perfluorinated bicyclononane, perfluorinated bicyclooctane, perfluorinated adamantane, perfluoromethyladamantane and perfluorodimethylbicyclo [3.3.1.]nonane, perfluorodimethylbicyclo[3.3.1.]nonane and perfluorotrimethylbicyclo[3.3.1.]nonane, perfluorotetrahydrodicyclopentadiene, perfluorinated bicyclononane, perfluorinated bicyclooctane, perfluorinated adamantane hydrocarbon, perfluoromethyladamantane and perfluorodimethylbicyclo[3.3.1]nonane, perfluorodimethyladamantane and perfluorotrimethylbicyclo[3.3.1.]nonane, and perfluorotetrahydrodicyclopentadiene and perfluorobicyclo[5.3.1]decane, and perfluorotributylamine (FC47), perfluorodecalin (PP5), perfluorotetrahydrofuran (FC80), perfluoroether (PID) [(CF$_3$)$_2$CFOCF$_2$(CF$_2$)$_2$CF$_2$OCF(CF$_3$)$_2$], perfluoroether (PIID) [(CF$_3$)$_2$CFOCF$_2$(CF$_2$)$_6$CF$_2$OCF(CF$_3$)$_2$],

perfluoropolymer (E3) [CF$_3$CHF(OCF$_2$CF)$_2$OCF$_2$CF$_2$CF$_3$], perfluroropolymer (E4) [CF$_3$CHF(OCF$_2$CF-)$_3$OCF$_2$CF$_2$CF$_3$], perfluoroetherpolyer (Fomblin Y/01), perfluorododecane, perfluorobicyclo[4.3.0]nonane, perfluorotrimethylcyclohexane, perfluoroisopropylcyclohexane, perfluoroendotetrahydrodicylopentadiene, perfluorobicyclo[5.3.0.]decane, perfluorotetramethylcyclohexane, perfluoro-1-methyl-4-isopropylcyclohexane, perfluoro-n-butylcyclohexane, perfluorodimethylbicyclo[3.3.1.]nonane, perfluoro-1-methyl adamantane, perfluoro-1-methyl-4-t-butylcyclohexane, perfluorodecahydroacenaphthlene, perfluorotrimethylbicyclo[3.3.1.]nonane, perfluoro-n-undecane, perfluorotetradecahydrophenanthrene, perfluoro-1,3,5,7-tetramethyladamantane, perfluorododecahydrofluorene, perfluoro-1,3-dimethyl adamantane, perfluoro-n-octylcyclohexane, perfluoro-7-methylbicyclo[4.3.0.]nonane, perfluoro-p-diisopropylcyclohexane, and perfluoro-m-diisopropylcyclohexane, and perfluorocyclocarbons such as perfluoro (methylcyclohexane), perfluoro (1,3-dimethylcyclohexane), perfluoro (decahydronaphthalene), perfluoro (decahydro-1-methylnaphthalene) and perfluoro (decahydrodimethylnaphthalene), or mixtures thereof, perfluorinated bicyclononane, perfluorinated bicyclooctane, perfluorinated adamantane hydrocarbon, perfluoromethyladamantane and perfluorodimethylbicyclo[3.3.1.]nonane, perfluorodimethyladamantane and perfluorotrimethylbicyclo[3.3.1.]nonane, perfluorotetrahydrodicyclopentadiene and perfluorobicyclo[5.3.0.]decane, perfluorotetrahydrodicyclopentadiene, perfluorinated bicyclononane, perfluorinated bicyclooctane, perfluorinated adamantane, perfluoromethyladamantane and perfluorotrimethylbicyclo[3.3.1.-]nonane, and perfluorotetrahydrodicyclopentadiene and perfluorobicyclo[5.3.0.]decane.

* * * * *